United States Patent
Geissler et al.

(12)

(10) Patent No.: US 6,310,261 B1
(45) Date of Patent: Oct. 30, 2001

(54) METHOD FOR THE PRODUCTION OF ALDEHYDES

(75) Inventors: Bernhard Geissler, Kirchheim; Michael Röper, Wachenheim; Edgar Zeller, Mannheim; Rocco Paciello, Bad Dürkheim; Jürgen Decker, Trier; Hartwig Voss, Frankenthal; Norbert Mahr, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/582,780

(22) PCT Filed: Jan. 14, 1999

(86) PCT No.: PCT/EP99/00187

§ 371 Date: Jul. 3, 2000

§ 102(e) Date: Jul. 3, 2000

(87) PCT Pub. No.: WO99/36382

PCT Pub. Date: Jul. 22, 1999

(30) Foreign Application Priority Data

Jan. 16, 1998 (DE) ............................................. 198 01 437

(51) Int. Cl.[7] .................................................. C07C 45/50
(52) U.S. Cl. .......................... 568/454; 568/451; 568/909
(58) Field of Search .................................. 568/451, 454, 568/909

(56) References Cited

U.S. PATENT DOCUMENTS

| | | | |
|---|---|---|---|
| 3,594,424 | 7/1971 | Brader et al. | 260/604 |
| 4,235,744 | 11/1980 | Pesa et al. | 252/428 |
| 4,252,678 | 2/1981 | Smith | 252/430 |
| 4,528,403 | 7/1985 | Tano et al. | 268/454 |
| 5,387,719 | 2/1995 | Kneuper et al. | 568/455 |
| 5,389,719 | 2/1995 | Takekoshi | 524/784 |
| 5,696,297 | 12/1997 | Kneuper et al. | 568/454 |
| 5,723,680 | 3/1998 | Kormann et al. | 568/455 |
| 5,846,453 | 12/1998 | Mohr et al. | 252/331 |
| 5,919,987 | 7/1999 | Kneuper et al. | 568/451 |

FOREIGN PATENT DOCUMENTS

| | | |
|---|---|---|
| 2 227 546 | 1/1974 | (DE) . |
| 26 04 545 | 8/1977 | (DE) . |
| 3338340 | 5/1984 | (DE) . |
| 32 27 704 | 3/1989 | (DE) . |
| 44 35 688 | 4/1996 | (DE) . |
| 196 03201 | 7/1997 | (DE) . |
| 196 08559 | 9/1997 | (DE) . |
| 588 225 | 3/1994 | (EP) . |
| 695 734 | 2/1996 | (EP) . |
| 82/03856 | 11/1982 | (WO) . |
| 95/25080 | 9/1995 | (WO) . |
| 96/16012 | 3/1996 | (WO) . |
| 97/28113 | 8/1997 | (WO) . |
| 97/30016 | 8/1997 | (WO) . |

OTHER PUBLICATIONS

New Syntheses with Carbon Monoxide, pp 38–57, Falbe (1980).
New Syntheses with Carbon Monoxide, pp 95–100,Falbe (1980).
Chem.Ber.102,2238–2240 (1969).
TetLtr. No.29, 3261–3266, 1968.
Hydroncarbon Processing Jun. 1975, 83–91;Cornils et al.
Mac.Symp.105,179–183(1996)Liu.

*Primary Examiner*—Sreeni Padmanabhan
(74) *Attorney, Agent, or Firm*—Keil & Weinkauf

(57) ABSTRACT

The invention relates to a method for the production of aldehydes or aldehydes and alcohols by hydroformylation of olefins in the presence of a complexing catalyst homogeneously dissolved in a reaction mixture, containing a metal of Group VIIIa of the periodic table of the elements and a phosphorus-free, polydentate nitrogen compound suitable for complex formation as ligand at temperatures ranging from 50 to 100° C. and pressures from 20 to 1,000 bar and recirculating the catalyst complex in the hydroformylation reaction, wherein a) derivatized polyamines are used that are substantially non-water soluble and suitable for complex formation and have a mean molecular weight of more than 1,000 Dalton and at least 10 nitrogen atoms; b) the catalyst complex remaining in the bottom of the distillation column and the excess ligands obtained from the reaction mixture are recirculated totally or partially in the hydroformylation once the hydroformylation reaction and the separation or partial separation by distillation of the aldehydes and the alcohols has been completed; c) continues or at least batchwise evacuation of at least part of the high boiler from the bottom of the distillation of the reaction mixture is then carried out.

11 Claims, 4 Drawing Sheets

METHOD FOR THE PRODUCTION OF ALDEHYDES

This is the U.S. National Stage Application of PCT/EP99/00187.

The present invention relates to a process for preparing aldehydes and alcohols by hydroformylation of olefins in the presence of catalyst complexes comprising a metal of group VIII of the Periodic Table of the Elements and as ligand a phosphorus-free, high molecular weight modified polyamine which is essentially insoluble in water and recycling of the catalyst complex remaining in the bottoms from the distillation of the reaction mixture to the hydroformylation reaction.

The hydroformylation of olefins using carbon monoxide and hydrogen in the presence of transition metal catalysts has already been studied very well. Although α-olefins can be hydroformylated very well using rhodium-containing phosphine-modified catalysts (cf. J. Falbe, Ed.: New Syntheses With Carbon Monoxide, Springer, Berlin 1980, p. 55 ff), this catalyst system is not very suitable for internal and branched internal olefins nor for olefins having more than 7 carbon atoms (cf. Falbe, p. 95 ff). Thus, internal carbon-carbon double bonds are only hydro- formylated very slowly in the presence of such a catalyst. Since the hydroformylation product is generally separated from the catalyst homogeneously dissolved in the reaction system by distillation and the boiling point of the aldehyde formed in the hydroformylation increases with increasing number of carbon atoms and chain length to temperatures at which the rhodium-phosphine-containing catalyst decomposes, this hydroformylation method is not economical for the hydroformylation of olefins having more than 7 carbon atoms.

In contrast, internal and branched internal olefins can be advantageously hydroformylated using "naked" rhodium, i.e. using rhodium compounds which are not modified with phosphorus-containing ligands such as phosphines or phosphites and are homogeneously dissolved in the hydroformylation medium. Such rhodium catalysts which are not modified with phosphines or phosphites and their suitability as catalyst for the hydroformylation of the abovementioned classes of olefins are known (see Falbe l.c., p. 38 ff). The terms "naked rhodium" or "naked" rhodium catalysts are used in this application for rhodium hydroformylation catalysts which, in contrast to conventional rhodium hydroformylation catalysts, are not modified with phosphorus-containing ligands such as phosphine or phosphite ligands under the conditions of the hydroformylation. Ligands in this sense do not include carbonyl or hydrido ligands. In the specialist literature (see Falbe l.c., p. 38ff), it is assumed that the rhodium compound $HRh(CO)_4$ is the catalytically active rhodium species in hydroformylation using "naked rhodium catalysts", although this has not been unambiguously proven owing to the many chemical reactions occurring in parallel in the hydroformylation zone. It is only for the sake of simplicity that use is also made of this assumption here. The "naked" rhodium catalysts are formed under the conditions of the hydroformylation reaction from rhodium compounds, e.g. rhodium salts such as rhodium(III) chloride, rhodium (III) nitrate, rhodium(II) acetate, rhodium(III) acetylacetonate, rhodium(III) sulfate or rhodium(III) ammonium chloride, from rhodium chalcogenides, such as rhodium(III) oxide or rhodium(III) sulfide, from salts of rhodium-oxygen acids, for example the rhodates, from rhodium-carbonyl compounds such as dicarbonyl- rhodium acetylacetonate or cyclooctadienerhodium acetate or cyclooctadienerhodium chloride in the presence of $CO/H_2$ mixtures which are generally referred to as synthesis gas. The procedure for hydroformylations using "naked" rhodium is described, for example, in the following references: U.S. Pat. No. 4,400,547; DE-A 33 38 340; DE-A 26 04 545; WO 82/03856; Chem. Ber. 102, 2238 (1969); Tetrahedron Lett. 29, 3261 (1968); Hydrocarbon Process. 85–86 (1975), EP-A 588 225, WO 95/25080, EP-A 695 734, WO 96/16012, WO 97/30016, DE-A 19608559, EP-A 885 183.

However, hydroformylation using "naked" rhodium also has the disadvantage that, as a result of the thermal stresses in the distillative work-up of the hydroformylation product, the thermolabile rhodium catalyst (cf. U.S. Pat. No. 4,400, 547) is partly decomposed to metallic rhodium which deposits on the walls of the reactor and pipes. The precipitated rhodium metal cannot be returned to the hydroformylation reaction since it cannot be converted into the catalytically active rhodium compound under the hydroformylation conditions. The rhodium losses resulting from this chemical behavior of the "naked" rhodium catalysts have hitherto prevented greater industrial use of this process.

DE-A 33 38 340 and U.S. Pat. No. 4,400,547 describe processes for hydro-formylation by means of "naked rhodium catalysts" in which a phosphine or phosphite is added to the reaction product from the hydroformylation to prevent precipitation of rhodium. These phosphorus compounds form phosphine or phosphite complexes with the rhodium catalyst and thus protect it from thermal decomposition during the course of the distillative work-up of the hydroformylation product. After the distillation is complete, the rhodium-containing distillation bottoms are treated with an oxidizing agent so that the rhodium is set free in catalytically active form from the phosphine or phosphite complexes in question and the phosphine or phosphite ligands are oxidized to the corresponding phosphine oxides and phosphates which do not form rhodium complexes under hydroformylation conditions. The oxidized distillation bottoms are then reused as catalyst for the hydroformylation. The oxidized phosphorus compounds formed in the oxidation generally do not interfere in the hydroformylation, although the process does result in accumulation of the oxidized phosphorus compounds in this hydroformylation circuit. Apart from these oxidized phosphorus compounds, the high-boiling components (e.g. aldol condensation products of the aldehydes) also accumulate in the catalyst circuit in this method of operation since they cannot be distilled off with the products and thus need to be bled off from the catalyst circuit.

According to U.S. Pat. No. 4,252,678, homogeneous, colloidal metal clusters of the elements rhodium, ruthenium, osmium and iridium which are bound to a polymer are used as catalysts for hydroformylation. Polymers which are mentioned as being usable for this purpose are vinyl polymers containing alkenyl, phosphine, phosphine oxide, arsine, isonitrile and isocyanate groups, in particular copolymers of styrene, of ethylene and their derivatives with butadiene, isoprene, cyclopentadiene, p-styryldiphenylphosphine and p-styryldiphenylphosphine oxide. The preparation of these metal clusters by thermal decomposition of carbonyl clusters of the metals in question is very complicated, which is why this process has not been able to become established.

Liu et al (Macromol. Symp. 105, 179 (1996)) describe the hydroformylation of propylene using rhodium clusters bound to polyvinylpyrrolidone which are colloidally dispersed in water. Since polyvinylpyrrolidone is not soluble in the hydroformylation medium, it is necessary when using this catalyst to carry out the reaction in a two-phase system of water/organic hydroformylation medium, as a result of which valuable high-pressure reaction space in the reactor is occupied by water, resulting in an unsatisfactory space-time yield based on the total reactor volume. In addition, these catalysts are very air-sensitive and are irreversibly deactivated if they come into contact with air during catalyst recycling.

Finally, U.S. Pat. No. 3,594,425 discloses a process for hydroformylation in which phosphorus-free, low molecular weight polyamines, including low molecular weight polyamines modified with alkylene oxides, are used as ligands. The specific poly- amines described all have a molecular weight of less than 300. Although it is indicated that the polyamine ligands open up the opportunity of recycling the catalyst complex with the distillation bottoms to the hydroformylation reaction, the use of the polyamines described there has the disadvantage that they are relatively volatile and, particularly in the hydroformylation of higher olefins, at least part of them gets into the distillate fraction of the reaction product. Furthermore, the catalyst complexes containing these low molecular weight polyamine ligands when subjected to strong thermal stress during the work up of the hydroformylation product by distillation, so that part of the catalyst metal is deposited. This process can thus not be carried out economically on an industrial scale.

It is an object of the present invention to find ligands which make possible an industrially applicable process for the hydroformylation of olefins with recycling of catalyst, which process is universally applicable and, particularly in the hydroformylation of higher olefins, allows complete separation and thus virtually loss-free recycling of the catalyst and the ligand and does not have the other disadvantages mentioned, e.g. precipitation of metallic rhodium or ligand losses on distillation.

We have found that this object is achieved by a process for preparing aldehydes or aldehydes and alcohols by hydroformylation of olefins in the presence of a catalyt complex which is homogeneously dissolved in the reaction mixture and comprises a metal of gorup VIIIa of the Periodic Table of the Elements and as ligand a phosphorus-free, polydentate nitrogen compound capable of complex formation, at from 50 to 100° C. and pressures of from 20 to 1000 bar, and recycling of the catalyst compled to the hydroformulation reaction, wherein a) the ligands used are modified polyamines which are essentially insoluble in water, are capable of complex formation and have a mean molecular weight of greater than 1000 dalton and contain at least 10 nitrogen atoms, b) after the hydroformylation reaction is complete and the aldehydes and alcohols have been separated or partially separated from the reaction mixture by distillation, the catalyst complex and excess ligand remaining in the distillation bottoms are completely or partially recycled to the hydroformylation and c) at least part of the high boilers are bled off, continuously or at least batchwise, from the bottoms from the distillation of the reaction mixture.

In particular, that this object is achieved by a process for preparing aldehydes or aldehydes and alcohols by hydroformylation of olefins in the presence of a catalyst complex which is homogeneously dissolved in the reaction mixture and comprises a metal of group VIIIa of the Periodic Table of the Elements and as ligand a phosphorus-free, polydentate nitrogen compound capable of complex formation, at from 50 to 100° C. and pressures of from 20 to 1000 bar, and recycling of the catalyst complex to the hydroformylation reaction, wherein a) the polyamine ligands used are polyethylenimines consisting essentially of units of the formula I

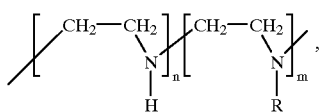

where the sum of m+n is at least 10 and the ratio of m/m+n is from 0.01 to 1 and R are identical or different alkyl, cycloalkyl, aryl, aralkyl or alkanoyl groups having up to 30 carbon atoms or hydroxyalkyl(poly) oxyalkylene groups having up to 500 oxyalkylene units, b) after the hydroformylation reaction is complete and the aldehydes and alcohols have been separated or partially separated from the reaction mixture by distillation, the catalyst complex and excess ligand remaining in the distillation bottoms are completely or partially recycled to the hydroformylation and c) at least part of the high boilers are bled off, continuously or at least batchwise, from the bottoms from the distillation of the reaction mixture.

For the purposes of the present invention, the term "modified polyamines which are essentially insoluble in water and are capable of complex formation" refers to polymeric polyamines whose amino groups have been alkylated, arylated, amidated or alkoxylated by reaction with, for example, alkylating, arylating, amidating or alkoxylating agents, or else are, as a result of chemical degradation reactions, e.g. hydrolysis or hydrogenolysis, of polymeric starting polyamines which are completely alkylated, arylated, amidated or alkoxylated on their amino groups, substituted by alkyl, aryl, alkanoyl or alkoxyl groups, to such an extent that these polymeric polyamines become essentially insoluble in water but soluble in the reaction mixture of the hydroformylation reaction and at least part of the nitrogen atoms of the amino groups is still available for complex formation with the metal of group VIIIa. Such modified polyamines can be produced, for example, from polyethyleneimine or polyvinylamine or precursor compounds of polyvinylamine, e.g. polyvinylformamide, by means of the abovementioned reactions. In the process of the present invention, preference is given to using modified polyamines based on polyethyleneimine, in particular alkylated, arylated, amidated or alkoxylated polyethyleneimine derivatives.

Suitable ligands to be used according to the present invention are, in particular, polyethylenimines consisting essentially of units of the formula III

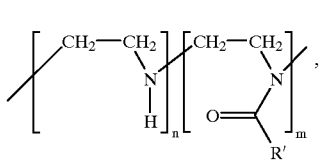

where the radical R' is alkyl having from 1 to 30 carbon atoms, referably from 1 to 21 carbonyl atoms, the sum of n and m is at least 10 and the ratio of m/m+n is from 0.01 to 1.

Further suitable ligands are polyethylenimines consisting essentially of units of the formula IV

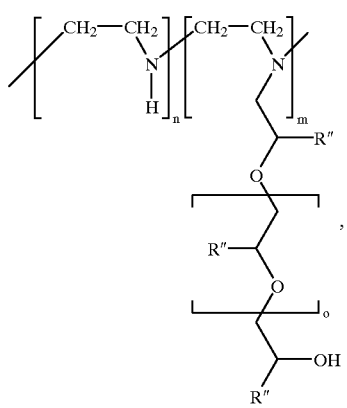

IV where R" is hydrogen or low molecular weight alkyl, i.e. a $C_1$–$C_{12}$-alkyl group, preferably a C1–C4-alkyl group, the sum of n and m is at least 10 and the ratio of m/m+n is from 0.01 to 1 and o can be from 0 to 500. These compounds are referred to as alkoxylated polyethylenimines and are described in DE-A 44 35 688 and DE-A 22 27 546. The contents of this prior literature, particularly with regard to the preparation of the polyamines, are expressly incorporated by reference into the present description.

Further ligands which are suitable according to the present invention are polyethyleneimines which consist essentially of units of the formula V

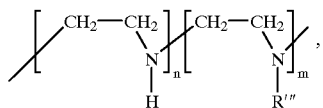

V where R''' are identical or different groups selected from among substituted or unsubstituted $C_1$–$C_{10}$-, preferably $C_1$–$C_{20}$-, in particular $C_1$–$C_{10}$-alkyl groups, $C_3$–$C_8$-cycloalkyl groups, $C_6$–$C_{12}$-aryl groups, preferably phenyl, or $C_7$–$C_{12}$-aralkyl groups, preferably the benzyl or phenylethyl, and the sum m+n is at least 10 and the ratio m/m+n is from 0.01 to 1. Among the polyethyenamine [sic] ligands of the formula V, preference is given to those in which R''' is a straight-chain or branched alkyl group. The polyethyleneimine ligands of the formula V can be prepared in a conventional way, e.g. from polyethyleneimine and the aldehydes or alcohols corresponding to R''' by reductive amination or by reacting polyethyleneimine with the alkyl, cycloalkyl, aryl or aralkyl halides corresponding to R''' in the presence of a base.

The molecular weight of the modified polyamine ligands of formula I, III, IV and V to be used according to the present invention is at least 1000 dalton, preferably more than 10,000 dalton. This is a mean weight average molar mass Mw, since the preparation of the polyamines and further reaction results, as is usual, in a broad molecular weight distribution.

The polyamine ligands to be used according to the present invention are completely soluble in the hydroformylation medium but are essentially insoluble in water. This means that, for example, not more than 1 g/l dissolves in water at room temperature and they cannot be extracted from the reaction mixture by means of water.

Particularly suitable compounds are those consisting essentially of units of the formulae III or IV

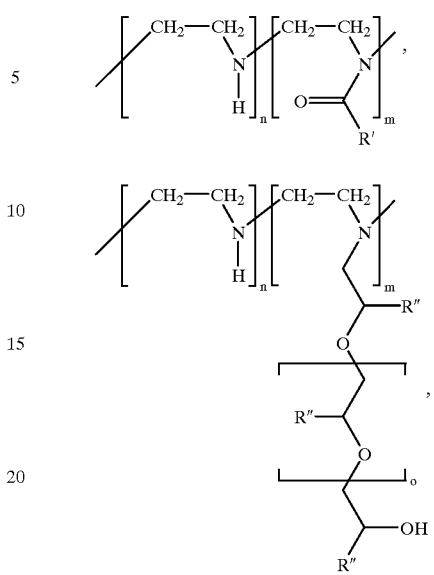

III

IV in which the sum of n+m is at least 10 and the ratio of m/m+n is from 0.01 to 1 and o is up to 500, R' is an alkyl group having from 5 to 30 carbon atoms and R" is hydrogen or a methyl group.

Specific examples of suitable compounds are:

Reaction products of polyethylenimine (prepared by polymerization of aziridine) having a mean molecular weight of from 200 to 2 million dalton with $C_1$–$C_{30}$-carboxylic acids, preferably $C_5$–$C_{30}$-carboxylic acids, in particular with carboxylic acids which are, owing to their favorable price, preferably available from natural sources, for example naturally occurring fatty acids or mixtures thereof or naphthenic acids, for example with formic acid, acetic acid, propionic acid, butyric acid, valeric acid, caproic acid, caprylic acid, capric acid, lauric acid, myristic acid, palmitic acid, steric acid, arachidic acid, behenic acid, oleic acid, linoleic acid, linolenic acid, erucic acid, etc., also with carboxylic acids which are inexpensively available from industrial sources, e.g. 2-ethylhexanoic acid and 2-propyl-heptanoic acid, where the degree of amidation is from 30 to almost 100%, based on the amidatable amino groups. Such polyethyleniminamides can be prepared, for example, by the method of DE-A 37 27 704 by reaction of polyethyleneimine with the appropriate carboxylic anhydrides or esters.

Further examples are reaction products of the abovementioned polyethylenimine having from 1 to 500 mol of ethylene oxide and/or propylene oxide and/or 1,2-butylene oxide per monomer unit of the polyethylenimine, as are described in DE-A 44 35 688.

Under hydroformylation conditions, metal compounds, in particular metal salts of group VIIIa of the Periodic Table of the Elements and the ligands to be used according to the invention form, in situ, novel hydroformylation catalyst complexes of the formula II

 $L(M(CO)_yH_z)$    II, where L is a ligand in the form of a modified polyamine which is essentially insoluble in water, is capable of complex formation, contains at least 10 nitrogen atoms and has a mean molecular weight of greater than 1000 dalton, preferably greater than 10,000 dalton, in particular a ligand consisting essentially of units of the formula I

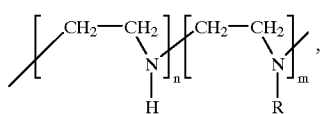

I where the sum of m+n is at least 10 and the ratio of m/m+n is from 0.01 to 1 and R are identical or different alkyl, cyclo-alkyl, aryl, aralkyl or alkanoyl gorups having up to 30 carbon atoms or hydroxyalkyl(poly)oxyalkylene groups having from 1 to 500 oxyalkylene units, M is an element of group VIIIa of the Periodic Table of the Elements, in particular rhodium or ruthenium, particularly preferably rhodium, y is from 1 to 4 and z is from 0 to 2.

Suitable olefins for the hydroformylation are any olefins, e.g. those having from 4 to 24 carbon atoms, in particular olefins having from 4 to 14 carbon atoms.

The olefins can be straight-chain or branched and can contain α-olefinic and/or internal double bonds. Specific examples which can be used in the process of the present invention are 1-octene, 1-dodecene, 1-tetradecene, trimeric and tetrameric propylene or dimeric, trimeric and tetrameric butylene. Likewise, it is possible to hydroformylate unsaturated oligomers of other olefins, e.g. hexene oligomers, likewise cooligomers of various olefins. The aldehydes formed from these olefins serve as precursors for the preparation of plasticizer alcohols and surfactants which can be produced therefrom by hydrogenation in a manner known per se. The olefins used for the hydroformylation can be prepared by many industrial processes as are described, for example, in Weissermel, Arpe: Industrielle Organische Chemie, pp. 67–86, Verlag Chemie, Weinheim, 1994.

The hydroformylation is carried out in a manner known per se at from 50° C. to 200° C., preferably from 70 to 180° C. and in particular from 80 to 170° C., and pressures of from 5 to 600 bar, preferably from 10 to 400 bar and in particular from 20 to 300 bar. The catalyst is generally formed in situ by addition of a compound containing the metal of group VIIIa of the Periodic Table of the Elements and an excess, e.g. a from 2 to 1000 molar excess, preferably a 4- to 500-fold and in particular a 10- to 100-fold molar excess, of the ligand, preferably that of the formula I, calculated on the basis of monomer units of the polyamine, so that the catalyst complexes of the formula II form under the reaction conditions. Since the catalysts used according to the present invention have not only a hydroformylation activity but also a certain hydrogenation activity, products of value formed are not only the aldehydes but also the alcohols corresponding to these aldehyes.

For further details, reference may be made to pertinent literature on hydroformylation, e.g. Falbe (see above).

The product from the hydroformylation stage is depressurized before being worked up by distillation. This results in liberation of unreacted synthesis gas which can be recycled to the hydroformylation. The same applies to the unreacted olefin which goes into the gas phase on depressurization and can, if desired after removal of inert hydrocarbons present therein by distillation, likewise be recycled to the hydroformylation. The distillation of the depressurized hydroformylation product is generally carried out at pressures of from 0.1 to 1000 mbar absolute, preferably from 1 to 500 mbar and particularly preferably from 10 to 200 mbar.

The temperature which has to be set in the distillation is dependent on the type of hydroformylation product and distillation apparatus used. In general, any distillation appa- ratuses can be used for the process of the present invention. However, preference is given to using apparatuses which incur low capital costs and allow as low as possible a distillation temperature, e.g. thin film evaporators. wiped film evaporators or falling film evaporators, since the aldehydes formed can undergo secondary reactions, e.g. aldol condensations, in the reaction product at elevated temperatures. Since this distillation serves essentially to separate the hydroformylation products aldehyde and alkyl and any other low boilers still present, e.g. unreacted olefin and inerts, from high-boiling condensation products of the aldehydes, referred to as high boilers, and the catalyst and excess ligand, it can be advantageous to subject the hydroformylation products and any olefins and inerts separated off in this way to a further purification by distillation, which can be carried out in a conventional manner.

An essential combination feature of the process of the present invention is the recycling of the catalyst complex and the excess ligand from the distillation residue of the reaction mixture. It is possible here either to a) recycle all of the distillation bottoms containing the catalyst and excess ligand or b) precipitate the catalyst and excess ligand by means of a solvent in which the catalyst and the excess ligand are insoluble or virtually insoluble and recycle only the precipitation product or c) isolate the catalyst and excess ligand by ultrafiltration of the distillation bottoms and recycle the retentate or d) the high boilers separate the high boilers present in the distillation bottoms from the catalyst and excess ligand by means of steam distillation and recycle only the distillation bottoms comprising catalyst and excess ligand obtained after the steam distillation to the hydroformylation reaction.

If method (a) is employed, it is advantageously used in combination with methods b) and/or c) and/or d) to avoid accumulation of high boilers in the circuit.

Those skilled in the art will know that, as an alternative to the methods b), c) and d) for avoiding an accumulation of high boilers in the reaction mixture of the hydroformylation, it is also possible to bleed off art of the distillation bottoms from the process from time to time and pass them to the further work-up for recovery of the group VIIIa metal and, if desired, the ligand used. In such a procedure, it goes without saying that the amount of group VIIIa metal and ligand bled off has to be replaced by feeding a corresponding amount of these compounds into the hydroformylation reaction.

Method a)

Preference is given to using those ligands according to the invention which have a vapor pressure at 25° C. of less than $10^{-5}$ mbar, preferably less than $10^{-6}$ mbar. This means that the polyamine ligand has a boiling point which is sufficiently high for all of the ligand-group-VIIIa-metal complex and all of the ligand not required for complex formation to remain in the distillation bottoms during distillation of the reaction product so that the bottoms from this distillation can be recycled to the reaction together with fresh olefin.

This process surprisingly leads to excellent results in hydro-formylation with distillative work-up of the reaction product, since the ligands to be used are very good stabilizers for the thermolabile catalyst and, owing to their low vapor pressure, remain quantitatively in the distillation bottoms and losses of the ligand and also fo the metal component of the catalyst can Thus be largely avoided, even when a very inexpensive distillation with a low number of theoretical plates, e.g. thin film evaporation or falling film evaporation, is used.

Since all high-boiling by-products are returned to the reaction in this variant of the process, a certain degree of accumulation of the high boilers occurs and it becomes necessary to bleed off high boilers continuously or batchwise. This can be achieved, for example, by, at least at intervals, separating the catalyst complex and the excess ligand from the distillation bottoms by means of one of the variants b), c) and d) described below and discarding the remainder consisting predominantly of high boilers.

Method b)

An essential requirement for this method of precipitation of the catalyst complex and the excess ligand is a solvent which is miscible over a wide range with the organic constituents of the distillation bottoms from the reaction product but in which the catalyst complex and the ligand are insoluble or almost insoluble so that it becomes possible, by selecting the type and amount of the solvent, to precipitate the catalyst complex and the ligand which can, after being separated off by decantation or filtration, be recycled to the hydroformylation, preferably in the form of a solution, e.g. dissolved in the olefin being fed to the reaction.

Suitable solvents include a large number of polar solvents, especially those containing

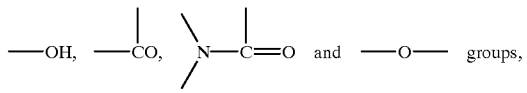

i.e. alcohols, ketones, amido or ethers, preferably acetone, tetrahydrofuran, dimethylformamide, dimethylacetamide, N-alkylpyrrolidones, glycols, methanol, ethanol, n-propanol, isopropanol and any mixtures of these with or without water.

The type and amount of solvent to be employed can be determined for the individual case by those skilled in the art by means of a few simple tests. In general, the amount of solvent is kept as small as possible so that the cost of recovery is as low as possible. Accordingly, the amount required is, as a rule, from 1 to 50 times, preferably from 3 to 15 times, the volume of the distillation bottoms.

Method c)

As a result of the large difference in the molecular weights of the catalyst complex and excess ligand on the one hand and the high boilers remaining in the distillation bottoms on the other hand, it is also possible to separate catalyst complex and ligand from the high boilers by ultrafiltration. For this purpose, the mean molecular weight of the ligand is more than 1000 dalton, preferably more than 10,000 dalton.

The process can be carried out continuously or batchwise.

BRIEF DESCRIPTION OF THE DRAWING

In the continuous mode of operation (FIG. 1), the starting materials 1 are reacted in the presence of catalyst and ligand in the reactor R. The reactor output 2 is separated in a distillation apparatus K into a distillate stream 3 containing the oxo products and a residue stream 4. The catalyst-containing bottoms 4 are fed continuously to a membrane filtration unit M. In this membrane unit, the bottoms which contain high boilers (or a mixture of high boilers, starting materials and oxo products), catalyst and ligand are worked up. The high boilers (and possibly starting materials and oxo products) permeate through the membrane. The retentate stream 5 which is depleted in high boilers (and possibly starting materials and oxo products) and enriched in catalyst and ligand is recycled to the hydro-formylation.

In the batchwise mode of operation (FIG. 2), the starting materials 1 are similarly reacted in the presence of catalyst and ligand in the reactor R. At the end of the reaction, the reaction product is separated in a distillation apparatus K into a distillate stream 3 containing the oxo products and a residue stream 4. These catalyst-containing bottoms from the distillation are collected in the container B. At the end of the distillation, the contents of the container can be worked up as a batch in the membrane filtration unit M. At the end of the ultrafiltration, the distillation bottoms which have been depleted in high boilers (and possibly starting materials and oxo products) and enriched in catalyst and ligand are recycled to the reactor for the next hydroformylation batch.

Figure 3:
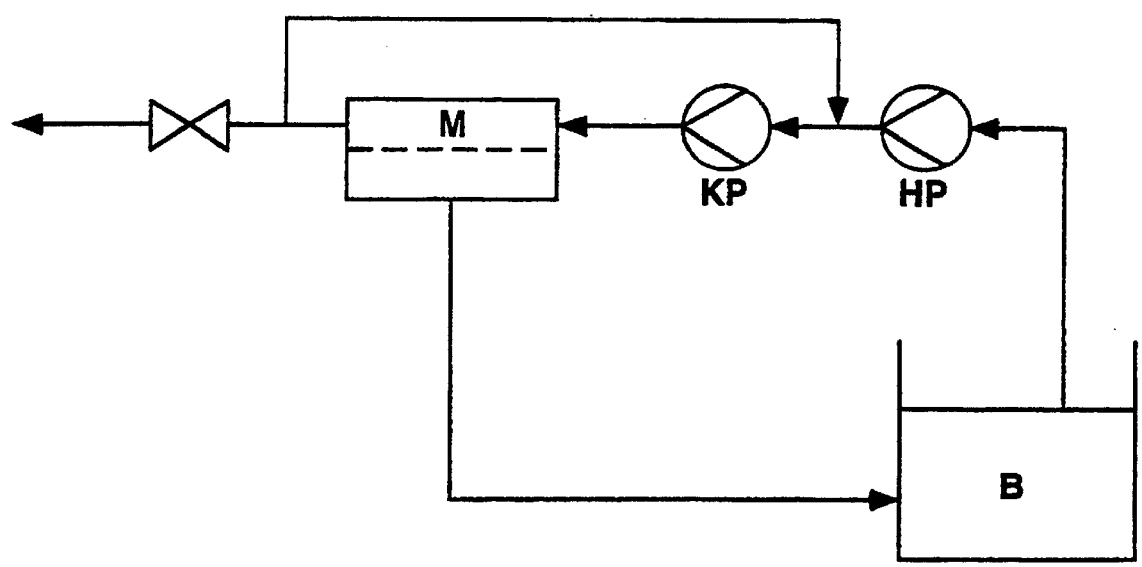
Figure 4:
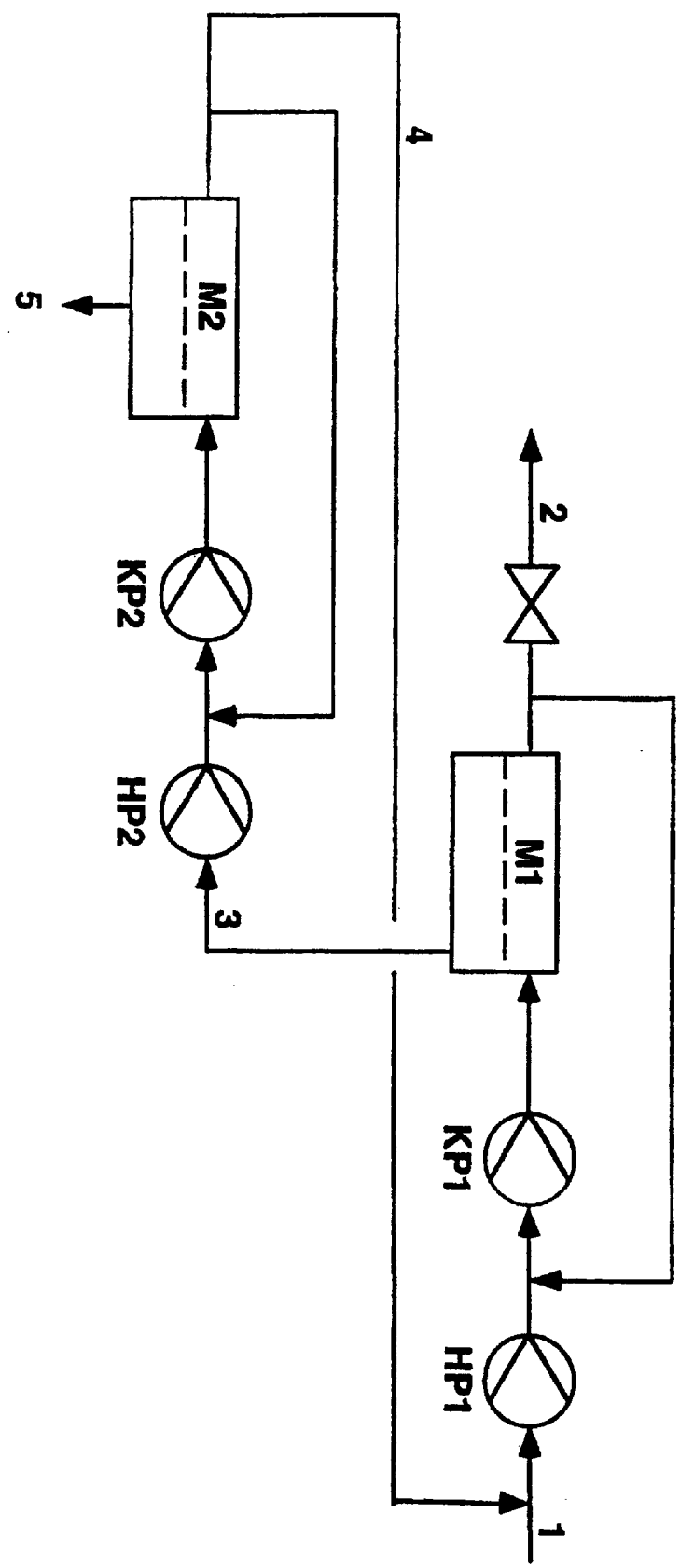

The ultrafiltration can be carried out in one stage (FIG. 3) or a plurality of stages (preferably in two stages as shown in FIG. 4). In each stage, the feed solution is brought to the filtration pressure in a pressure pump HP; by means of a second pump KP, flow over the membrane, i.e. wetting of the membrane, is then ensured by recirculation of part of the retentate stream. In the multistage variant, the permeate stream from one stage is passed to the downstream stage and the retentate stream from this downstream stage is passed to the previous stage. This work-up of the permeate makes it possible to achieve better retention of the catalyst and the ligand.

In the case of a multistage unit, the various stages can be equipped with the same membrane or with different membranes.

The ultrafiltration is preferably carried out at transmembrane pressures of from 0.5 to 20 bar, preferably from 2 to 12 bar, and at temperatures up to 200° C., depending on membrane material. The flow velocity over the membrane in the module is from 1 to 10 m/s, preferably from 1 to 4 m/s. The catalyst concentration in the feed solution to the membrane is from 5 to 2000 ppm, the polymer concentration, i.e. the concentration of free polymer ligand, is from 1 to 12% by weight.

All membranes which are stable in the system are suitable for the ultrafiltration. The separation limit of the membranes is from 500 to 200,000 dalton. Suitable membrane materials are polymers (1), ceramic materials (2), glass, metal or ceramic on metal (3). Examples of such membranes are shown in the following table.

| Type | Designation | Material | Separation limit | Manufacturer |
| --- | --- | --- | --- | --- |
| (1) | MPF-U20-S | Polysulfone | 20,000 dalton | Membran Products Kiryat Weizmar |
| (2) | K00X1040 | ZiO$_2$ on Al$_2$O$_3$—TiO$_2$ | 15,000 dalton | Tech-Sep |
| (2) | | TiO$_2$ | 5000 to 10,000 dalton | Inocermic Gesellschaft für Innovative Keramik mbH |
| (2) | | TiO$_2$ | 5000 dalton | Société des Céramiques Techniques |
| (3) | | TiO$_2$ on stainless steel | | Graver Chemical Company |

Method d)

A further possible way of removing high-boiling condensation products of the aldehydes is to separate them from the distillation bottoms by means of steam distillation. The steam distillation of the distillation bottoms can be carried out discontinuously, i.e. batchwise, or continuously, either in the distillation apparatus itself or in a separate steam distillation apparatus. For example, in the discontinuous embodiment of the process, the distillation bottoms can, before being recycled to the hydroformylation, be completely or partially freed of high-boiling condensation products by passing steam through them or the distillation bottoms can, depending on the formation of high boilers, be subjected to a steam distillation from time to time in a separate apparatus. The continuous embodiment of this method can be carried out, for example, by continuously feeding the distillation bottoms or part of the distillation bottoms before their return to the hydroformylation to a steam distillation apparatus and their freeing them completely or partially of high boilers. It is likewise possible to carry out the distillative work-up of the hydroformylation produc continuously in the presence of steam from the beginning in order to separate the high boilers from the catalyst and the ligand at the same time as the aldehyde and the alcohol are separated off. It goes without saying that in such a procedure the products of value have to be freed of the high boilers and if necessary water in a downstream fractionation or distillation apparatus.

The steam distillation is generally carried out in a conventional way by passing steam into the distillation bottoms comprising high boilers and subsequently condensing the steam distillates.

The steam is advantageously passed through the distillation bottoms in such a way that it does not condense in the distillation bottoms. This can be achieved by selection of the pressure and/or temperature conditions under which the steam distillation is carried out. Here, it is possible to employ either reduced pressure or, when using superheated steam, superatmospheric pressure. In general, the steam distillation is carried out at from 80 to 200° C. and a pressure of from 1 mbar to 10 bar, preferably from 5 mbar to 5 bar. The amount of steam 10 passed through the distillation bottoms generally corresponds, based on the high-boiling condensation products of the aldehydes (high boilers) present in the bottoms, to a weight ratio of steam:high boilers of from 10:1 to 1:10. After completion of the steam distillation, the distillation bottoms which have in this way been completely or partially freed of high boilers and comprise catalyst and excess ligand can be recycled to the hydroformylation.

As already mentioned in the case of method a), it may also be advantageous to combine methods a) and b) or a) and c) or a) and d).

In all cases, the process of the invention leads to improved results compared to the prior art, since the ligands to be used according to the present invention now allow both the very decomposition-sensitive "naked" rhodium to be stabilized and the catalyst complex and excess ligand to be recycled to the hydroformylation reaction in a manner which can be utilized on an industrial scale.

EXAMPLES (A) Preparation of the Modified Polyamine Ligands

Example 1

General example of the ethoxylation of a polyamine, described here for a polyethylenimine having a mean molecular weight of 5000.

Example 1a)

Monoalkoxylation of a polyethylenimine in water (first stage)

An autoclave was charged with 43 g of a polyethylenimine having a weight average molecular weight of about 5000 together with 43 g of water. At from 90 to 100° C. and a pressure of at most 4 bar, 44 g of ethylene oxide were then added while stirring over a period of 30 minutes. Stirring was continued for 1 hour at this temperature and 20 g of 50% strength by weight aqueous KOH solution were added. The water was completely distilled off under reduced pressure (down to about 10 mbar) while increasing the temperature to 120° C. over a period of 5 hours.

Example 1b

Further alkoxylation (second stage)

In an autoclave, the precursor from Example 1a was reacted with about 480 g of ethylene oxide at 130–140° C. and a pressure of up to about 4.5 bar.

Example 2

General example for the propoxylation of a polyamine, described here for a polyethylenimine having a mean molecular weight (weight average) of 20,000.

Example 2a

Monoalkoxylation of a polyethylenimine in water (first stage) and azeotropic distillation of the water after addition of xylene An autoclave was charged with 43 g of a polyethylenimine having a weight average molecular weight of about 20,000 together with 43 g of water. At from 90 to 100° C. and a pressure of at most 4 bar, 58 g of propylene oxide were then added while stirring over a period of 30 minutes. Stirring was continued for 1 hour at this temperature, the mixture was cooled to about 80° C., 20 g of 50% strength by weight aqueous KOH solution and 100 g of xylene were added and all water was removed by azeotropic distillation.

Example 2b

Further alkoxylation (second stage) in the presence of xylene

In an autoclave, the precursor from Example 2a was reacted with 4234 g of propylene oxide at 130–140° C. and a pressure of up to about 4.5 bar.

Example 3

Synthesis of a polyethylenimine amidated to an extent of 50 mol% (based on amidatable amino groups) by stearic acid In a 4 liter capacity flask which was fitted with a stirrer, thermometer and a facility for working under nitrogen, 258 g of polyethylenimine having a mean molecular weight ($M_w$) of about 25,000 g/mol were heated to 140° C. under a stream of nitrogen. Over a period of 30 minutes, 853.5 g of stearic acid were added a little at a time. The reaction temperature was increased to 180° C., whereupon the mixture became yellow and foamed. The water formed was distilled off continuously. After 18 hours, the mixture was allowed to cool, giving 1059 g of a pale yellow solid. The reaction product dissolved in xylene to give a clear solution but was insoluble in water. No residual acid content could be detected by titration with tetrabutylammonium hydroxide in xylene.

Example 4

Synthesis of a polyethylenimine amidated to an extent of 60 mol% (based on amidatable amino groups) by lauric acid In a 2 liter capacity four-neck flask fitted with stirrer, dropping funnel, temperature measurement and a distillation attachment, 297 g (1.48 mol) of lauric acid were melted at 100° C. under a gentle stream of nitrogen. The melt was heated to 150° C. and 212.5 g of a 50% strength solution of a polyethylenimine (2.47 mol) having a mean molecular weight (Mw) of 460,000 was added via the dropping funnel. The rate of dropwise addition was selected so that the temperature was maintained at from 150 to 155° C. and the water introduced was distilled off. The mixture was subsequently heated for 15 hours at 180° C., thus distilling off the water formed in the amidation reaction. The melt was cooled to 100° C., taken from the reactor and comminuted at room temperature. This gave 364 g of a yellow solid.

The reaction product dissolved in xylene and tetrahydrofuran to give a clear solution but was insoluble in water. No residual acid content could be detected by titration with tetrabutyl-ammonium hydroxide in xylene.

(B) Hydroformylation

Example 5

Hydroformylation of butene dimer using an Rh catalyst comprising an amidated polyethylenimine (from Example 3)

5.01 mg of dicarbonylrhodium acetylacetonate (0.0194 mmol), 1.0 g of amidated polyethyleneimine from Example 3, 100 g of butene dimer (0.891 mmol) and $CO/H_2$ were heated at 150° C. The desired pressure of 280 bar was set by means of a 1:1 mixture of $CO/H_2$. After 3.5 hours, the autoclave was cooled, vented and emptied. Analysis of the reaction mixture by means of gas chromatography using an internal standard and correction factors indicated a conversion of butene dimer of 98%, a yield of nonanals of 85.6% and a yield of nonanols of 9.5%.

Example 6

Hydroformylation of 1-octene using an Rh catalyst comprising an amidated polyethylenimine (from Example 3)

12.53 mg of dicarbonylrhodium acetylacetonate (0.0485 mmol), 1.0 g of amidated polyethyleneimine, 99 g of 1-octene (0.882 mol) and $CO/H_2$ were heated at 100° C. A pressure of 280 bar was set by means of a 1:1 mixture of $CO/H_2$. After 5 hours, the autoclave was cooled, vented and emptied. Analysis of the reaction mixture by means of GC, using an internal standard and correction factors, indicated a conversion of 1-octene of 99.7%, a yield of nonanals of 99.3% (n-content=53.6%) and a selectivity for the formation of internal olefins of 0.18%.

Example 7

Hydroformylation of 1-dodecene using an Rh catalyst comprising an amidated polyethylenimine (from Example 3)

12.53 mg of dicarbonylrhodium acetylacetonate (0.0485 mmol), 1.0 g of amidated polyethyleneimine, 99 g of 1-dodecene (0.588 mol) and $CO/H_2$ were heated at 100° C. A pressure of 280 bar was set by means of a 1:1 mixture of $CO/H_2$. After 5 hours, the autoclave was cooled, vented and emptied. Analysis of the reaction mixture by means of GC, using an internal standard and correction factors, indicated a conversion of 1-dodecene of 98.4%, a yield of tridecanals of 97.1%, a yield of tridecanols of 0.5%, a selectivity to tridecanals of 98.6% (n-content=52.7%) and a selectivity to tridecanols of 0.5%.

Example 8

Hydroformylation of a mixture of 1-dodecene and 1-tetradecene using an Rh catalyst comprising an amidated polyethylenimine (from Example 4)

5.01 mg of dicarbonylrhodium acetylacetonate (0.0194 mmol), 1.0 g of amidated polyethyleneimine, 100 g of a mixture of 1-dodecene and 1-tetradecene in a ratio of 2/1 and $CO/H_2$ were heated at 100° C. The desired pressure of 90 bar was set by means of a 1:1 mixture of $CO/H_2$. After 5 hours, the autoclave was cooled, vented and emptied. Analysis of the reaction mixture by means of GC, evaluated using percentage areas, indicated a conversion of 1-dodecene of 99%, a conversion of 1-tetradecene of 99% and a total yield of alcohols and aldehydes of 97.5%.

Example 9

Hydroformylation of n-dodecene (butene trimer) using an Rh catalyst comprising an amidated polyethylenimine (from Example 3)

12.53 mg of dicarbonylrhodium acetylacetonate (0.0485 mmol), 1.0 g of amidated polyethyleneimine, 99 g of n-dodecene (0.588 mol) and $CO/H_2$ were heated at 150° C. A pressure of 280 bar was set by means of a 1:1 mixture of $CO/H_2$. After 5 hours, the autoclave was cooled, vented and emptied. Analysis of the reaction mixture by means of GC, determined using % areas, indicated a conversion of n-dodecene of 93.8%, a yield of tridecanals of 92.4% and a yield of tridecanols of 0.7%.

Example 10

Hydroformylation of internal n-dodecenes using an Rh catalyst comprising an amidated polyethylenimine (from Example 3) 12.53 mg of dicarbonylrhodium acetylacetonate (0.0485 mmol), 1.0 g of amidated polyethyleneimine, 99 g of dodecenes having internal double bonds (0.588 mol) and $CO/H_2$ were heated at 130° C. A pressure of 280 bar was set by means of a 1:1 mixture of $CO/H_2$. After 5 hours, the autoclave was cooled, vented and emptied. Analysis of the reaction mixture by means of GC, using an internal standard and correction factors, indicated a conversion of internal dodecenes of 98.2%, a yield of tridecanals of 93.9% and a yield of tridecanols of 2.7%.

Example 11

Hydroformylation of butene dimer using an Rh catalyst comprising a propoxylated polyethylenimine (from Example 2)

5 mg of dicarbonylrhodium acetylacetonate (0.0194 mmol), 9.7 g of propoxylated polyethylenimine, 95 g of butene dimer (0.85 mol), 5 g of Palatinol® C (dibutyl phthalate) and $CO/H_2$ were heated at 150° C. A pressure of 280 bar was set by means of a 1:1 mixture of $CO/H_2$. After 5 hours, the autoclave was cooled, vented and emptied. Analysis of the reaction mixture by means of GC, using an internal standard and correction factors, indicated a conversion of 87.7%, a yield of nonanals of 78.1% and a yield of nonanols of 4.1%.

Example 12

Hydroformylation of butene dimer using an Rh catalyst comprising a propoxylated polyethylenimine (from Example 2)

5 mg of dicarbonylrhodium acetylacetonate (0.0194 mmol), 9.7 g of propoxylated polyethylenimine, 95 g of butene dimer (0.85 mol), 5 g of Palatinol® C (dibutyl phthalate) and $CO/H_2$ were heated at 130° C. A pressure of 280 bar was set by means of a 1:1 mixture of $CO/H_2$. After 5 hours, the autoclave was cooled, vented and emptied. Analysis of the reaction mixture by means of GC, using an internal standard and correction factors, indicated a conversion of 78.1%, a yield of nonanals of 72.0% and a yield of nonanols of 0.9%.

Example 13

Hydroformylation of isobutene using an Rh catalyst comprising an amidated polyethylenimine (from Example 3)

7.1 mg of dicarbonylrhodium acetylacetonate (0.074 mmol), 0.385 g of amidated polyethylenimine, 47.5 g of Texanol®, 31.5 g of isobutene (0.56 mol) and CO/H$_2$ were heated at 130° C. A pressure of 280 bar was set by means of a 1:1 mixture of CO/H$_2$. After 3 hours, the autoclave was cooled, vented and emptied. Analysis of the reaction mixture by means of GC, using an internal standard and correction factors, indicated a conversion of isobutene of 100%, a yield of 3-methylbutanol of 96% and a yield of pivalaldehyde of 0.2%.

(C) Separation and Recycling of the Catalyst

Example 14

Batchwise hydroformylation, distillation and precipitation of catalyst and of excess ligand and recycling to the hydroformylation Example 5 was repeated using 10 times the amount of starting materials. After the reaction was complete, the reaction product was distilled at 150° C. and 10 mbar. The distillation was stopped when a residual amount of 100 g remained. The concentration of amidated polyethylenimine in the distillation residue was 12.7% and the Rh concentration was 249 ppm.

The distillation bottoms were admixed with 10 times their mass of acetone and 0.2 times their mass of water. The mixture was stirred for 30 minutes and held at 7° C. for 10 hours. The precipitate formed was filtered off.

The filtrate was freed of water and acetone by distillation and the distillation residue was analyzed:

rhodium content=2.5 ppm nitrogen content=200 ppm

The precipitate from the precipitation was again admixed with the same amount of butene dimer and the hydroformylation was repeated under the conditions of Example 5. The conversion of butene dimer was 96.3%, the yield of nonanals was 84.4% and the yield of nonanols was 9.4%.

Example 15

Continuous hydroformylation of butene dimer, distillation, precipitation of the catalyst and the excess ligand and recycling to the hydroformylation Butene dimer was hydroformylated continuously using the catalyst system rhodium/polyethylenimine (50% amidation by stearic acid as described in Example 3). The reaction product was fractionated in a wiped film evaporator, the distillate and the distillation bottoms were analyzed and the distillation bottoms were recycled, together with fresh butene dimer, to the hydroformylation.

Olefin feed/return of distillation bottoms (mass ratio): 3/1; temperature of the hydroformylation 150° C.; pressure: 280 bar of a 1:1 mixture of CO/H$_2$; temperature of the wiped film evaporator: 130° C.; pressure in the wiped film evaporator: 10 mbar.

rhodium content of the distillation bottoms=185 ppm of Rh nitrogen content of the distillation bottoms=0.36% content of high boilers in the distillation bottoms=90%

10% of the total amount of the distillation bottoms was taken out and admixed with 9 times its mass of acetone and 0.2 times its mass of water. The mixture was stirred for 30 minutes and held at 7° C. for 10 hours. The precipitate obtained was filtered off and the filtrate was freed of water and acetone by distillation. Analysis of the distillation residue indicated a rhodium content of 3.1 ppm and a nitrogen content of 280 ppm.

The filtration residue was dissolved in a further part of the distillation bottoms from the continuous hydroformylation and reintroduced into the reaction. This precipitation was repeated every 24 hours. After 17 days of continuous hydroformylation without further addition of rhodium and ligand, a conversion of butene dimer of 91.1%, a selectivity to aldehydes of 88.7% and a selectivity to alcohols of 8.7% were obtained before treatment of the distillation bottoms was commenced.

After the experiment had been carried out continuously for 17 days, a conversion of butene dimer of 89.5%, a selectivity to aldehydes of 91.3% and a selectivity to alcohols of 6.7% were determined.

Example 16

Two-stage precipitation

A two-stage precipitation was carried out on the distillation residue obtained as described in Example 14 to separate catalyst and excess ligand as completely as possible from the distillation bottoms:

The filtrate from the precipitation, obtained as in Example 14, was not evaporated but a further 2% by mass of water were added to it. The solution was cooled to −30° C. and stirred. After one hour, a small amount of a precipitate was filtered off. The filtrate was freed of water and acetone by distillation and the distillation residue was analyzed. The rhodium content was now 0.7 ppm and the nitrogen content was 60 ppm.

Similar results are obtained when the distillation residues from the hydroformylation of other olefins as described in the other hydroformylation examples are treated by precipitation and recycled.

Example 17

Continuous hydroformylation of butene dimer using continuous ultrafiltration of the distillation bottoms and recycling of the retentate comprising the catalyst and excess ligand to the hydroformylation Continuous hydroformylation of butene dimer using a modified polyethylenimine as described in Example 3.

Figure 1:
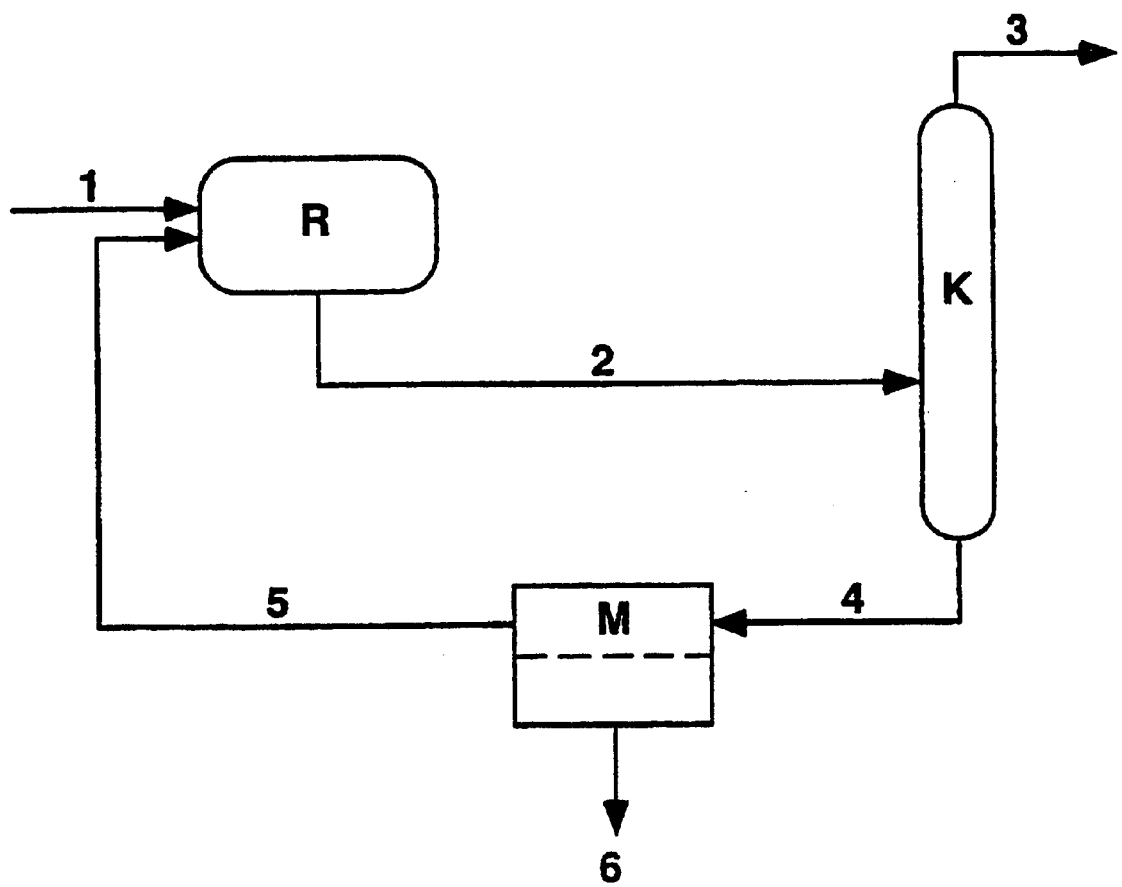

In the reactor R as shown in FIG. 1, butene dimer was hydroformylated continuously using the catalyst system rhodium/amidated polyethylenimine. The reaction product 2 was fractionated in a wiped film evaporator K. The product stream 3 was taken off at the top and the distillation bottoms 4 were worked up continuously in the membrane filtration unit M. The retentate from the ultrafiltration 5 was recycled to the reaction. The losses of catalyst and ligand, which permeate in a very small amount together with the high boilers, were made up by metering correspondingly small amounts of catalyst and ligand into the reactor.

Temperature of the hydroformylation: 150° C. Pressure: 280 bar of a 1:1 mixture of CO/H$_2$ Temperature of the wiped film evaporator: 130° C.

Pressure in the wiped film evaporator: 10 mbar

The distillation bottoms 4 contained 200 ppm of Rh and 5% by weight of amidated polyethylenimine. This solution was subjected to ultrafiltration at 100° C., a transmembrane pressure of 10 bar and a flow velocity of 2 m/s in a membrane module equipped with a membrane (ZrO$_2$, 15,000 dalton) from Tech-Sep.

The results of the membrane filtration are shown in the following table.

| Streams as shown in FIG. 1 | m (kg/h) | $c_{rhodium}$ (ppm) |
|---|---|---|
| 4 (bottoms) | 9 | 200 |
| 5 (retentate) | 6 | 294 |
| 6 (filtrate) | 3 | 12 |

Under the experimental conditions, the specific permeate flux was 20 kg/m$^2$h. The retention of rhodium was 95.9%.

This procedure was repeated a number of times and led, on average, to a butene dimer conversion of 89.5% at an aldehyde selectivity of 89.3% and an alcohol selectivity of 8%.

Similar results were obtained when distillation residues from the hydroformylation of other olefins were treated by ultrafiltration and recycled.

Example 18

Batchwise hydroformylation with subsequent ultrafiltration of the distillation bottoms and recycling of the retentate comprising the catalyst and excess ligand to the hydroformylation Batchwise hydroformylation of butene dimer using an amidated polyethylenimine as described in Example 3.

Example 5 was repeated using 10 times the amount of starting materials and, after the reaction was complete, the reaction product was distilled at 150° C. and 10 mbar. The distillation was stopped when 200 g of residue remained. The rhodium concentration of the residue was 125 ppm and the concentration of amidated polyethylenimine was 6.3%.

The distillation residue was then worked up in a single-stage membrane filtration unit equipped with the membrane MPF-U20-S from Membran Products Kiryat Weizmar.

Filtration occurred at 40° C., 9 bar and the flow velocity was 2 m/s. The results of the membrane filtration are shown in the following table.

Figure 2:
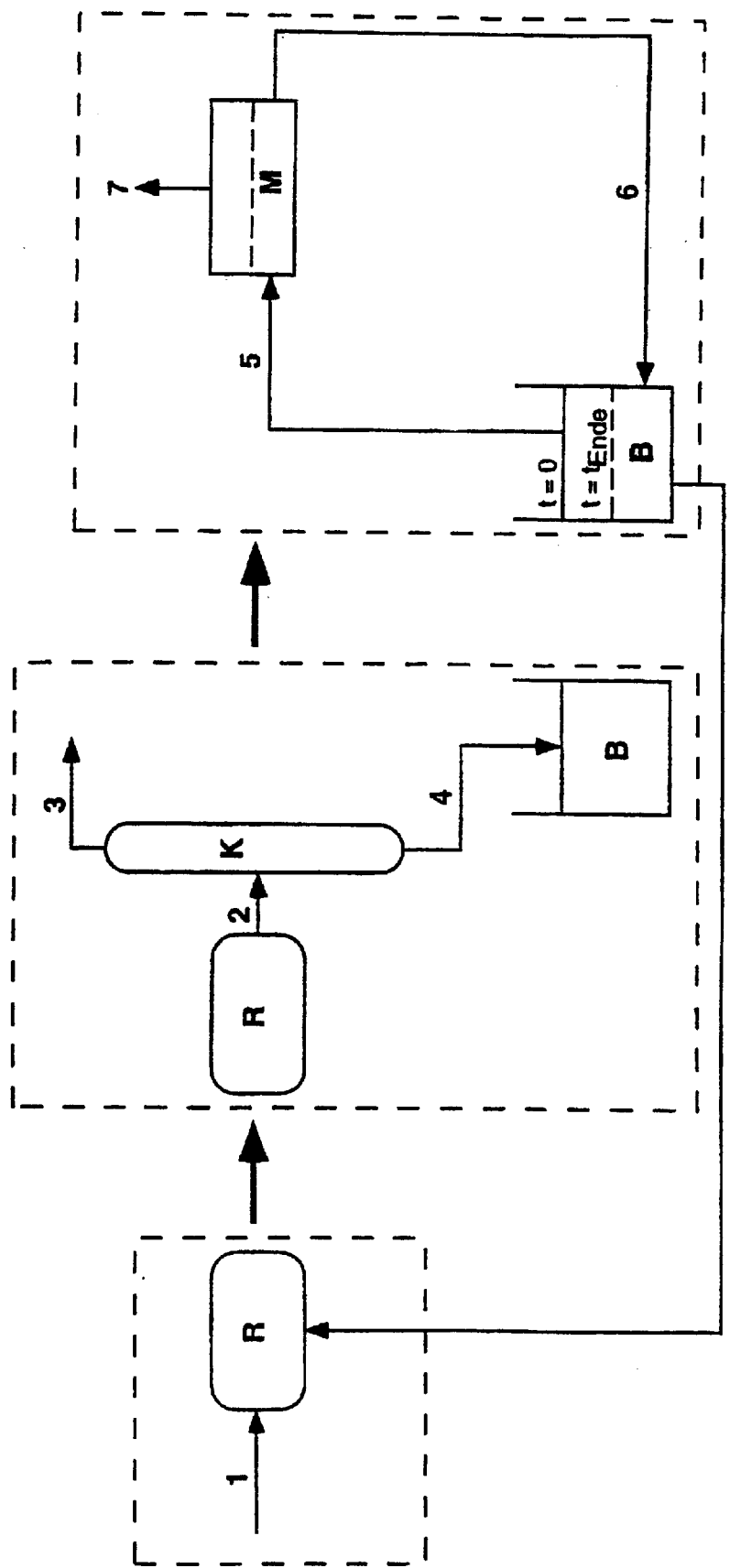

| FIG. 2 | m (g) | $c_{rhodium}$ (ppm) |
|---|---|---|
| B1 (t = 0) (bottoms) | 200 | 125 |
| B1 (t = $t_{end}$) (retentate) | 100 | 242 |
| B2 (filtrate) | 100 | 8 |

Under the conditions employed, the specific permeate flux was 1 kg/M$^2$h. The retention of rhodium was 96.7%.

The retentate (100 g) was admixed with the same amount of butene dimer and the hydroformylation was repeated under the conditions of Example 5. The conversion of butene dimer was 97.8%, the yield of nonanals was 84.5% and the yield of nonanols was 9.3%.

We claim:

1. A process for preparing aldehydes or aldehydes and alcohols by hydroformylation of olefins in the presence of a catalyst complex which is homogeneously dissolved in the reaction mixture and comprises a metal of group VIIIa of the Periodic Table of the Elements and as ligand a phosphorus-free, polydentate nitrogen compound capable of complex formation, at from 50 to 200° C. and pressures of from 20 to 1000 bar, and recycling of the catalyst complex to the hydroformylation reaction, wherein a) the ligands used are modified polyamines which are essentially insoluble in water, are capable of complex formation, have a mean molecular weight of greater than 1000 dalton and contain at least 10 nitrogen atoms, b) after the hydroformylation reaction is complete and the aldehydes and alcohols have been separated or partially separated from the reaction mixture by distillation, the catalyst complex and excess ligand remaining in the distillation bottoms are completely or partially recycled to the hydroformylation and c) at least part of the high boilers are bled off, continuously or at least batchwise, from the bottoms from the distillation of the reaction mixture, where the catalyst and excess ligand are precipitated by means of a solvent in which the catalyst and the excess ligand are insoluble or virtually insoluble and only the precipitation product is recycled to the hydroformylation, and/or the catalyst and excess ligand are recovered by ultrafiltration of the bottoms from the distillation and the retentate stream which is depleted in high boilers and enriched in catalyst and ligand is recycled to the hydroformylation, and/or the high boilers present in the bottoms from the distillation are separated from the catalyst and excess ligand by means of steam distillation and only the distillation bottoms comprising catalyst and excess ligand from the steam distillation are recycled to the hydroformylation reaction.

2. A process as claimed in claim 1, wherein the polyamines used are polyethylenimines consisting essentially of units of the formula I,

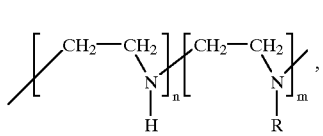

I where the sum of m+n is at least 10 and the ratio of m/m+n is from 0.01 to 1 and R are identical or different alkyl, cycloalkyl, aryl, aralkyl or alkanoyl groups having up to 30 carbon atoms or hydroxyalkyl(poly)oxyalkylene groups having up to 500 oxyalkylene units.

3. A process as claimed in claim 1, wherein the ligand used is a modified polyamine which has a mean molecular weight of more than 1000 dalton.

4. A process as claimed in claim 1, wherein the ligand used is a modified polyamine which has a vapor pressure of less than 10$^{-5}$ mbar at 25° C.

5. A process as claimed in claim 1, wherein the ligand used is a modified polyamine which is, both as free ligand and in the form of its complex with the metal of group VIIIa, completely soluble in the reaction mixture of the hydroformylation but is insoluble or only sparingly soluble in a polar solvent which is miscible with the reaction mixture of the hydroformylation or mixtures of a plurality of such solvents, the ligand and the complex of the ligand with the metal of group VIIIa is precipitated from the bottoms or part of the bottoms from the distillation of the reaction mixture from the hydroformylation by addition of this solvent and the ligand and complex of the ligand with the metal of group VIIIa which have been precipitated in this way are recycled to the hydroformylation reaction.

6. A process as claimed in claim 5, wherein use is made of a polar solvent selected from the group consisting of acetone, tetrahydrofuran, dimethylformamide, dimethylacetamide, N-alkylpyrrolidones, glycols, methanol, ethanol, n-propanol, isopropanol and mixtures thereof with or without water.

7. A process as claimed in claim 1, wherein, after distilling off or partially distilling off the aldehydes and alcohols, the catalyst complex and excess ligands are isolated by ultrafiltration and recycled to the hydroformylation.

8. A process as claimed in claim 1, wherein, while or after distilling off or partially distilling off the aldehydes and alcohols, the distillation bottoms comprising the catalyst complex and excess ligand are subjected to a steam distillation and the distillation bottoms comprising the catalyst complex and excess ligand are then completely or partially recycled to the hydroformylation.

9. A process as claimed in claim 1, wherein olefins having more than 3 carbon atoms are hydroformylated.

10. A process as claimed in claim 1, wherein olefins having from 4 to 24 carbon atoms are hydroformylated.

11. A process as claimed in claim 1, wherein the hydroformylation and the subsequent distillative removal of the aldehydes and alcohols are carried out continuously, the major part of the bottoms comprising the catalyst, excess ligands and the high boilers are recycled to the hydroformylation reaction and a small part of the bottoms are bled off, the catalyst and excess ligand are isolated or obtained in enriched form therefrom by a process wherein the ligand used is a modified polyamine which is, both as free ligand and in the form of its complex with the metal of group VIIIa, completely soluble in the reaction mixture of the hydroformylation but is insoluble or only sparingly soluble in a polar solvent which is miscible with the reaction mixture of the hydroformylation or mixtures of a plurality of such solvents, the ligand and the complex of the ligand with the metal of group VIIIa is precipitated from the bottoms or part of the bottoms from the distillation of the reaction mixture from the hydroformylation by addition of this solvent and the ligand and complex of the ligand with the metal of group VIIIa which have been precipitated in this way are recycled to the hydroformylation reaction and are likewise recycled to the hydroformylation reaction.

* * * * *